United States Patent
Hao

(10) Patent No.: US 10,220,329 B2
(45) Date of Patent: Mar. 5, 2019

(54) ACID PURIFIER

(71) Applicant: Donghui Hao, Apex, NC (US)

(72) Inventor: Donghui Hao, Apex, NC (US)

(73) Assignee: AMERLAB SCIENTIFIC LLC, Fuquay Varina, NC (US)

( * ) Notice: Subject to any disclaimer, the term of this patent is extended or adjusted under 35 U.S.C. 154(b) by 0 days.

(21) Appl. No.: 15/764,433

(22) PCT Filed: Jan. 26, 2016

(86) PCT No.: PCT/CN2016/072207
§ 371 (c)(1),
(2) Date: Mar. 29, 2018

(87) PCT Pub. No.: WO2017/080113
PCT Pub. Date: May 18, 2017

(65) Prior Publication Data
US 2018/0280829 A1    Oct. 4, 2018

(30) Foreign Application Priority Data

Nov. 10, 2015   (CN) .......................... 2015 1 0760564
Nov. 10, 2015   (CN) .......................... 2015 1 0761218
Nov. 10, 2015   (CN) .......................... 2015 1 0761221

(51) Int. Cl.
*B01D 5/00*   (2006.01)
*B01L 3/16*   (2006.01)
(Continued)

(52) U.S. Cl.
CPC ......... *B01D 5/0051* (2013.01); *B01D 5/0063* (2013.01); *B01J 19/0013* (2013.01);
(Continued)

(58) Field of Classification Search
CPC ...... B01D 3/42; B01D 5/0051; B01D 5/0063; B01J 19/0013
See application file for complete search history.

(56) References Cited

U.S. PATENT DOCUMENTS 5,447,077 A * 9/1995 Lautenschlager .... B01D 1/0017
                                                       422/430
5,873,980 A    2/1999 Young
(Continued)

FOREIGN PATENT DOCUMENTS

CN      101428243 A    5/2009
CN      201625542 U    11/2010
(Continued)

OTHER PUBLICATIONS

International Search Report.

*Primary Examiner* — Jonathan Miller
(74) *Attorney, Agent, or Firm* — Na Xu; IPro, PLLC

(57) ABSTRACT

An acid purifier, comprising: a container (1) for an acid to be purified; a heater (2); a condenser (3) including a Peltier semiconductor cooler, a condenser body (600) and a refrigerant temperature sensor; a purified acid liquid collection bottle (4) connected with the condenser; a controller; an integrated liquid level control component (300) for the acid to be purified, connected with the container (1) for the acid to be purified, and arranged in such a way that a liquid level pipe (320), a liquid adding funnel (310) and a waste liquid discharge valve (330) are integrated; and an acid liquid temperature sensor (400, 500) arranged in the acid to be purified.

13 Claims, 8 Drawing Sheets

(51) Int. Cl.
    *B01J 19/00*    (2006.01)
    *G01N 1/34*    (2006.01)
    *G01N 1/40*    (2006.01)

(52) U.S. Cl.
    CPC ............... *B01L 3/16* (2013.01); *G01N 1/34* (2013.01); *G01N 2001/4033* (2013.01)

(56) References Cited

U.S. PATENT DOCUMENTS

| | | | | |
|---|---|---|---|---|
| 6,508,915 B1 * | 1/2003 | Osuda | ............... | B01D 3/42 |
| | | | | 159/44 |
| 7,474,971 B2 * | 1/2009 | Hu | ............... | G01N 33/2823 |
| | | | | 702/50 |
| 2008/0210384 A1 * | 9/2008 | Guthrie | ............... | B01D 1/222 |
| | | | | 159/6.1 |

FOREIGN PATENT DOCUMENTS

| | | | |
|---|---|---|---|
| CN | 202263412 | U | 6/2012 |
| CN | 203705007 | U | 7/2014 |
| CN | 103979497 | A | 8/2014 |
| CN | 105233897 | A | 1/2016 |
| CN | 105251547 | A | 1/2016 |
| CN | 105251548 | A | 1/2016 |
| CN | 205084757 | U | 3/2016 |
| CN | 205308369 | U | 6/2016 |
| CN | 205308370 | U | 6/2016 |
| DE | 20019875 | U1 | 3/2001 |

\* cited by examiner

ACID PURIFIER

TECHNICAL FIELD

The present disclosure generally relates to acid liquid purification, and more particularly, to an acid purification apparatus.

BACKGROUND

Laboratory trace and ultra-trace analysis often requires an ultra-pure acid, so an acid of ordinary purity needs to be slowly evaporated in a sub-boiling state and to be condensed and collected as a purer acid.

A purifier generally has a heating function, a temperature control function, a liquid level monitoring function and a condensation function, to perform heating, temperature control, liquid level monitoring and condensation as well as collection on an acid liquid.

In purifier design currently available in a market, there are usually shortcomings in aspects as follows:

1. Temperature Control:

(1) In a conventional solution, in order to avoid a temperature sensor from being easily corroded by high temperature strong acid, the temperature sensor is installed outside a container, to avoid contact with the strong acid; however, in such an installation mode, it is temperature of an outer wall of the container that is measured, which cannot reflect true temperature of the acid liquid, usually there is a difference of 5° C. to 20° C. between temperature of a solution and the temperature of the outer wall of the container, so a temperature measurement error is great.

(2) In the conventional solution, a temperature controller is a multi-position type, rather than a continuously adjustable type, which may only set a temperature value roughly and cannot set accurately.

2. Liquid Level Control:

(1) With respect to a liquid level of a raw acid liquid, in the conventional solution, the liquid level of a liquid level pipe is determined in a mode of visual inspection; once personnel forget to perform visual inspection in time, there will be a huge risk of dry burning or even breaking out of fire.

(2) With respect to a liquid level of a high-purity acid liquid, there is no automatic detection and control measure in the existing solution. Once the liquid level is overfilled, the acid liquid will spill out of a bottle and corrode surrounding objects.

3. Condensation Control and Heating Control:

(1) An air cooling mode or a tap water cooling mode is used in the existing solution. Both modes show no temperature indicating a cooling effect.

(2) Both modes are susceptible to influence of air temperature and tap water temperature conditions; once the air temperature or the water temperature rises, the cooling effect will be affected.

(3) A tap water cooling mode also has a risk of incapability of cooling down due to a lack of water supply.

(4) An infrared lamp or a resistance wire is used as a heat source in the existing solution, which is open flame and easily ignites an inflammable gas around;

(5) Once the temperature controller fails, the infrared lamp or the resistance wire will continue to heat, causing a great risk of burning down an instrument or even a laboratory fire.

SUMMARY

With respect to a current state of the prior art, the present disclosure has been made.

According to one aspect of the present disclosure, there is provided a purifier, comprising: a container for an acid to be purified, for containing an acid to be purified; a heater, for heating the container for the acid to be purified, to obtain hot acid steam; a condenser, configured to condense the hot acid steam; a purified acid liquid collection bottle connected with the condenser, for collecting condensed purified acid; and a controller, for controlling operation of respective components so as to perform an acid purification process, characterized by further comprising an integrated liquid level control component for the acid to be purified, connected with the container for the acid to be purified, and arranged in such a way that a liquid level pipe, a liquid adding funnel and a waste liquid discharge valve are integrated, the acid to be purified enters into the container for the acid to be purified, a liquid level of the liquid level pipe reflects a liquid level of the container for the acid to be purified, and the waste liquid discharge valve is capable of discharging a waste liquid when opened.

In one example, the heater is a PTC heater.

In one example, the purifier may further comprise: an aluminum plate provided on an upper surface of the PTC heater.

In one example, the purifier may further comprise: an acid liquid temperature sensor, provided inside the acid to be purified, for measuring temperature of the acid liquid to be purified; wherein, the controller sets a temperature threshold, receives the temperature measured by the acid liquid temperature sensor, compares the temperature with a temperature threshold, and correspondingly controls the PTC heater.

In one example, the acid liquid temperature sensor is a thermocouple-type temperature sensor, placed in a polytetrafluoroethylene (PTFE) capillary, the PTFE capillary is placed in a support tube, the support tube is placed in the container for the acid to be purified, and the PTFE capillary extends to the outside of the container for the acid to be purified through a connection hole on a wall of the container for the acid to be purified.

In one example, the PTFE capillary passes through an inner hole of the support tube, is wound around a tube coiler for one circle, and then enters into the support tube again.

In one example, the controller may continuously set the temperature thresholds.

In one example, the condenser includes a Peltier semiconductor cooler, a condenser body, and a refrigerant temperature sensor, "cold water" cooled in the Peltier semiconductor cooler, enters the condenser body by pressure of a water pump, to cool the acid steam in contact with an outer shell of the condenser body, "hot water" then enters into the Peltier semiconductor cooler through the water pump to be cooled, and then the process restarts and works circularly; and the refrigerant temperature sensor measures temperature of a refrigerant in the Peltier semiconductor cooler.

In one example, a bottom of the condenser body is a diaphragm having a thickness less than a predetermined threshold; the diaphragm is in contact with the hot acid steam to cool the hot acid steam; the condensed purified acid enters the purified acid liquid collection bottle through a drainage tube.

In one example, a middle portion of the condenser body is divided into two portions by a baffle, to guide a water flow direction, so that internal temperature is more uniform.

In one example, the refrigerant temperature sensor uses a capillary thermocouple; on tubing between the semiconductor cooler and the condenser body, a capillary thermocouple is inserted into the tubing and an insertion port is subjected to seal processing.

In one example, the purifier is placed inside a fume hood, but the semiconductor cooler and the controller are placed outside the fume hood.

In one example, the purifier may further comprise: a non-contact ultrasonic liquid level sensor, installed on an outer surface of the container and not in contact with a surface of the container, for automatically measuring the liquid level of the acid to be purified in the container for the acid to be purified, and sending a measured signal indicating the horizontal liquid level to the controller, wherein, the controller receives the signal indicating the liquid level, and sends a control signal when the signal indicating the liquid level is below a predetermined threshold, so as to control stopping an acid purification process.

In one example, the purifier may further comprise: a pressure sensor, for automatically sensing weight of the purified acid liquid collection bottle, and sending a signal indicating the weight to the controller; wherein, the controller receives the signal indicating the weight, and sends a control signal when the signal indicating that the weight exceeds a predetermined threshold, so as to control stopping the acid purification process.

In one example, the purified acid liquid collection bottle is placed on a tray, the tray is designed in a flanging manner, to prevent the acid liquid from dripping into the pressure sensor; and the pressure sensor is designed with a leak outlet, to allow the acid liquid to be discharged in a case where there is an acid liquid entering inside the sensor.

In one example, the pressure sensor is subjected to surface spraying of PTFE.

In one example, data transmission between all sensors and computers is performed by means of wireless communication.

The purifier according to this embodiment uses an integrated liquid level control component to be purified, which integrates the liquid level pipe, the liquid adding funnel and the waste liquid discharge valve into one, so it not only can have the liquid level observed, but also can serve as a funnel to add the liquid, and can discharge a waste liquid as well, which avoids a trouble that the funnel needs to be installed and uninstalled before and after adding the acid liquid, in a conventional solution that the funnel, the liquid level pipe and the waste liquid discharge valve are separated from each other, so as to avoid pollution in a funnel storage process.

According to one aspect of the present disclosure, there is provided an acid purifier, comprising: a container for an acid to be purified, for containing an acid to be purified; a heater, for heating the container for the acid to be purified, to obtain hot acid steam; a condenser, configured to condense the hot acid steam; a purified acid liquid collection bottle connected with the condenser, for collecting condensed purified acid; and a controller, for controlling operation of respective components so as to perform an acid purification process; an acid liquid temperature sensor, for measuring temperature of the acid liquid to be purified; wherein, the controller sets a temperature threshold, receives the temperature measured by the acid liquid temperature sensor, compares the temperature with a temperature threshold, and correspondingly controls the heater; the condenser includes a Peltier semiconductor cooler, a condenser body, and a refrigerant temperature sensor, "cold water" cooled in the Peltier semiconductor cooler, enters the condenser body by pressure of a water pump, to cool the acid steam in contact with an outer shell of the condenser body, "hot water" then enters into the Peltier semiconductor cooler through the water pump to be cooled, and then the process restarts and works circularly; and the refrigerant temperature sensor measures temperature of a refrigerant in the Peltier semiconductor cooler.

In one example, the heater is a PTC heater.

In one example, the acid purifier may further comprise: a thermal conductive pad provided on an upper surface of the PTC heater.

In one example, the thermal conductive pad is made of a pure aluminum material, with an area larger than a heating surface of the PTC heater, and is in close contact with a bottom of the container for the acid to be purified, and the heater and the thermal conductive pad are subjected to surface spraying of PTFE.

In one example, a bottom of the condenser body is a diaphragm having a thickness less than a predetermined threshold; the diaphragm is in contact with the hot acid steam to cool the hot acid steam; and the condensed purified acid enters the purified acid liquid collection bottle through a drainage tube.

In one example, a middle portion of the condenser body is divided into two portions by a baffle, to guide a water flow direction, so that internal temperature is more uniform.

In one example, the refrigerant temperature sensor uses a capillary thermocouple; on tubing between the semiconductor cooler and the condenser body, a capillary thermocouple is inserted into the tubing, and an insertion port is subjected to seal processing.

In one example, a top of the condenser body is sealed with a lid made of a PVDF material, with a silicon rubber seal ring sandwiched in between.

In one example, the acid purifier is placed inside a fume hood, but the semiconductor cooler and the controller are placed outside the fume hood.

In one example, the condenser body is made of a PTFE material.

In one example, the acid purifier further comprises a base, the container for the acid to be purified and the base use a nested connection design, to form a closed space between the two, and the entire PTC heater is installed inside the closed space.

In one example, the acid purifier may further comprise: a non-contact ultrasonic liquid level sensor, installed on an outer surface of the container and not in contact with a surface of the container, for automatically measuring the liquid level of the acid to be purified in the container for the acid to be purified, and sending a measured signal indicating the horizontal liquid level to the controller, wherein, the controller receives the signal indicating the liquid level, and sends a control signal when the signal indicating the liquid level is below a predetermined threshold, so as to control stopping the acid purification process.

In one example, the acid purifier may further comprise: a pressure sensor, for automatically sensing weight of the purified acid liquid collection bottle, and sending a signal indicating the weight to the controller; wherein, the controller receives the signal indicating the weight, and sends a control signal when the signal indicating that the weight exceeds a predetermined threshold, so as to control stopping the acid purification process.

In one example, the purified acid liquid collection bottle is placed on a tray, the tray is designed in a flanging manner, to prevent the acid liquid from dripping into the pressure sensor; and the pressure sensor is designed with a leak outlet, to allow the acid liquid to be discharged in a case where there is an acid liquid entering inside the sensor.

In one example, the pressure sensor is subjected to surface spraying of PTFE.

In one example, the controller includes a computer and a microcontroller, data transmission between all sensors and computers is performed by means of wireless communication.

The acid purifier according to the embodiment of the present disclosure has the condenser provided with the Peltier semiconductor cooler and the refrigerant temperature sensor, which has a stable cooling effect, without being influenced by temperature of the air and tap water, can accurately indicate a cooling effect, and provides a safe, stable and accurate cooling mode.

According to one aspect of the present disclosure, there is provided an acid purifier, comprising: a container for an acid to be purified, for containing an acid to be purified; a heater, for heating the container for the acid to be purified, to obtain hot acid steam; a condenser, configured to condense the hot acid steam; a purified acid liquid collection bottle connected with the condenser, for collecting condensed purified acid; a controller, for controlling operation of respective components so as to perform an acid purification process; an acid liquid temperature sensor, arranged in the acid to be purified, for measuring temperature of the acid liquid to be purified; wherein, the controller sets a temperature threshold, receives the temperature measured by the acid liquid temperature sensor, compares the temperature with a temperature threshold, and correspondingly controls the heater.

In one example, the acid liquid temperature sensor is a thermocouple-type temperature sensor, two thermocouple leads are placed in a polytetrafluoroethylene (PTFE) capillary, the PTFE capillary is placed in a support tube, the support tube is placed in the container for the acid to be purified, and the PTFE capillary extends to the outside of the container for the acid to be purified through a connection hole on a wall of the container for the acid to be purified.

In one example, a lower end of the support tube is connected with a tube coiler, and the PTFE capillary inside the support tube passes through an inner hole of the support tube and then gets out, is wound around the tube coiler for one circle and enters into the support tube through a hole of the support tube, then extends upward along the support tube, and finally passes through the hole of the support tube and the connection hole on a wall of the container for the acid to be purified, to extend outside the container for the acid to be purified, wherein, a thermocouple head portion is located within the one circle for which the PTFE capillary is wound, and the thermocouple head portion is in contact with the PTFE capillary.

In one example, the two thermocouple leads are brought into contact oppositely, seemingly as one lead, and the portions in opposite contact become a thermocouple head.

In one example, the acid liquid temperature sensor is a thermocouple-type temperature sensor, a surface of the thermocouple lead is enveloped by a PTFE envelope layer, and at a position of the thermocouple probe, a thermocompression method is used for tightly bonding the thermocouple probe to the PTFE envelope layer.

In one example, one or more sealing points are present on the thermocouple lead, and a thermo-compression method is used at the sealing point for tightly bonding the thermocouple lead with the PTFE envelope layer.

In one example, the controller is capable of continuously setting temperature thresholds.

In one example, the condenser includes a Peltier semiconductor cooler, a condenser body and a refrigerant temperature sensor, "cold water" cooled in the Peltier semiconductor cooler, enters the condenser body by pressure of a water pump, to cool the acid steam in contact with an outer shell of the condenser body, "hot water" then enters into the Peltier semiconductor cooler through the water pump again to be cooled, and then the process restarts and works circularly; and the refrigerant temperature sensor measures temperature of a refrigerant in the Peltier semiconductor cooler.

In one example, the bottom of the condenser body is a diaphragm having a thickness less than a predetermined threshold; the diaphragm is in contact with the hot acid steam to cool the hot acid steam; the condensed purified acid enters the purified acid liquid collection bottle through a drainage tube.

In one example, a middle portion of the condenser body is divided into two portions by a baffle, to guide a water flow direction, so that internal temperature is more uniform.

In one example, the refrigerant temperature sensor uses a capillary thermocouple; on tubing between the semiconductor cooler and the condenser body, a capillary thermocouple is inserted into the tubing, and an insertion port is subjected to seal processing.

In one example, the acid purifier is placed inside a fume hood, but the semiconductor cooler and the controller are placed outside the fume hood.

In one example, the acid purifier may further comprise: a non-contact ultrasonic liquid level sensor, installed on an outer surface of the container and not in contact with a surface of the container, for automatically measuring the liquid level of the acid to be purified in the container for the acid to be purified, and sending a measured signal indicating the horizontal liquid level to the controller, wherein, the controller receives the signal indicating the liquid level, and sends a control signal when the signal indicating the liquid level is below a predetermined threshold, so as to control stopping the acid purification process.

In one example, the acid purifier may further comprise: a pressure sensor, for automatically sensing weight of the purified acid liquid collection bottle, and sending a signal indicating the weight to the controller; wherein, the controller receives the signal indicating the weight, and sends a control signal when the signal indicating the weight exceeds a predetermined threshold, so as to control stopping the acid purification process.

In one example, the purified acid liquid collection bottle is placed on a tray, the tray is designed in a flanging manner, to prevent the acid liquid from dripping into the pressure sensor; and the pressure sensor is designed with a leak outlet, to allow the acid liquid to be discharged in a case where there is acid liquid entering inside the sensor.

In one example, the pressure sensor is subjected to surface spraying of PTFE.

In one example, the heater is a PTC heater.

In one example, the controller includes a computer as a host computer and a microcontroller as a slave computer, data transmission between all sensors and computers is performed by means of wireless communication.

The acid purifier according to the embodiment of the present disclosure has the temperature sensor arranged in the acid liquid, so that the measured temperature is equal to or substantially equal to the temperature of the acid liquid, which ensures accuracy of temperature measurement.

BRIEF DESCRIPTION OF THE DRAWINGS

These and/or other advantages of the present disclosure will become more apparent and understandable from the detailed description of the embodiments of the present disclosure in conjunction with the accompanying drawings, in which:

FIG. 9 (a) and FIG. 9(b) show a tridimensional view and a cross-sectional view of a purifier provided with an ultrasonic liquid level sensor 900 according to an embodiment of the present disclosure.

FIG. 10(a) shows a tridimensional schematic diagram of relative position relation between a pure acid solution collection bottle 4 and the pressure sensor and a relevant portion 1000 according to the embodiment of the present disclosure.

DETAILED DESCRIPTION

In order to make those skilled in the art better understand the technical solutions of the present disclosure, the present disclosure is further described in detail in conjunction with the drawings and specific embodiments.

First of all, it should be noted that, in the present text, terms "raw acid", "acid to be purified" and "to-be-purified acid" denote a same meaning as used herein, and refer to an acid solution which is fed to a purifier as a purification target. These terms are used interchangeably. Terms "purified acid" and "pure acid" denote a same meaning and are used interchangeably to refer to an acid solution obtained after purification process performed by the purifier.

Figure 1:
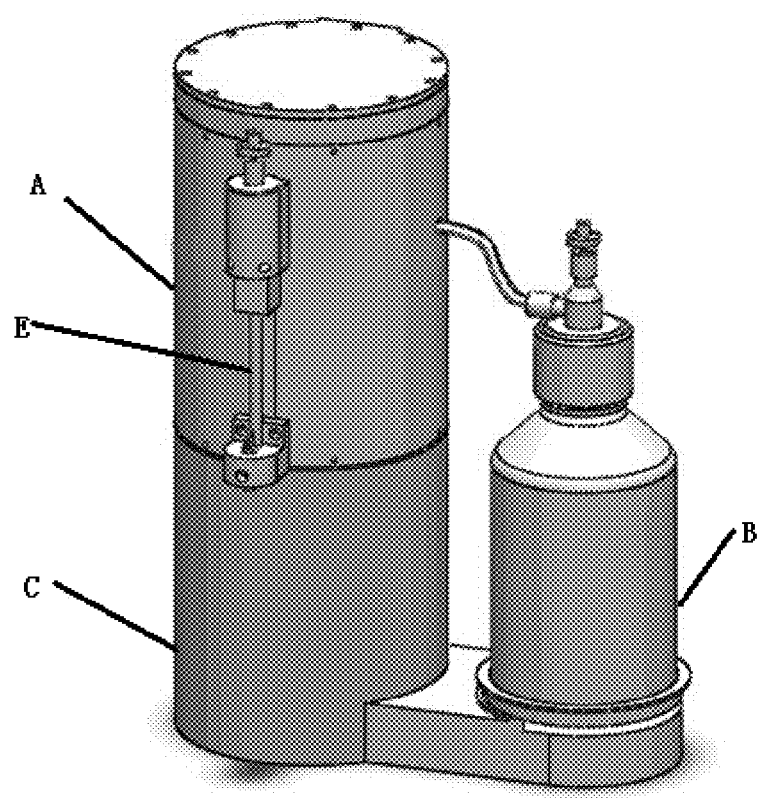
FIG. 1 shows a tridimensional schematic diagram of a purifier according to an embodiment of the present disclosure.

FIG. 1 shows a tridimensional schematic diagram of a purifier according to an embodiment of the present disclosure.

The exemplary purifier shown in FIG. 1 comprises a raw acid (i.e., a to-be-purified acid) relevant portion A of (including a container for the acid to be purified, a heater and a condenser, which will be described in detail hereinafter), a purified acid collection portion B, a base portion C and an integrated liquid level control component E for the acid to be purified, connected with the container for the acid to be purified. The raw acid (i.e., the to-be-purified acid) relevant portion A includes the container for the acid to be purified, the heater and the condenser, which will be described in detail hereinafter.

Figure 2:
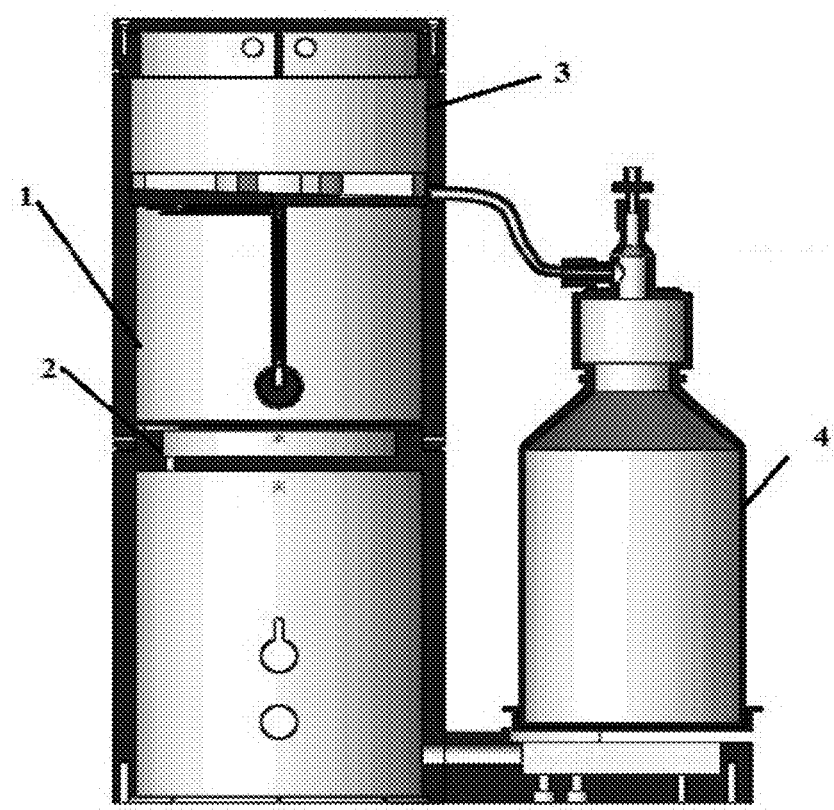
FIG. 2 shows a structural schematic diagram of the purifier according to the embodiment of the present disclosure.

FIG. 2 shows a structural schematic diagram of a purifier according to an embodiment of the present disclosure.

The purifier comprises a container 1 for an acid to be purified, a heater 2 and a condenser 3, a purified acid liquid collection bottle 4, an integrated liquid level control component for the acid to be purified (not shown in FIG. 2, a portion indicated by a reference sign E in FIG. 1), and a controller (not shown).

The container 1 for the acid to be purified is used for containing the acid to be purified (which is sometimes referred to herein as the raw acid, both interchangeably). The heater 2 heats the container for the acid to be purified, to obtain hot acid steam. The condenser 3 condenses the hot acid steam obtained by heating. The purified acid liquid collection bottle 4 is connected with the condenser, for collecting the condensed purified acid. The controller is used for controlling operation of respective components so as to perform an acid purification process.

In one example, the controller includes two portions, i.e., a host computer and a slave computer. The host computer may be a general-purpose computer such as a desktop computer, a notebook computer, a mobile terminal, or the like, in which software suitable for executing control is installed; the slave computer is, for example, a microcontroller or a dedicated programmable controller, etc., wherein, respective sensors in the purifier may send a signal to the slave computer, the slave computer processes and sends a relevant signal to the host computer, by wired or wireless means, and the host computer performs corresponding calculation, processing, judging, to transmit an instruction signal to the slave computer, and the slave computer gives commands to respective components, for example, closing down, starting, alarming, time setting, threshold setting, and the like. However, this mode is only an example, which may be adjusted or changed as required.

For convenience of description, hereinafter, sometimes the host computer is referred to as a "computer", and the slave computer as a "microcontroller".

In an example shown in FIG. 2, a temperature sensor 5 is placed inside the container 1 for the acid to be purified, the temperature sensor 5 is placed within the container 1 for the acid to be purified, and brought into contact with the acid liquid for measuring temperature of the acid liquid to be purified, the controller sets a temperature threshold, receives the temperature measured by the acid liquid temperature sensor, compares the measured temperature with the temperature threshold, and controls the heater accordingly. Hereinafter, an implementation mode of a built-in temperature sensor will be described in detail.

Below, an overall workflow of the purifier according to the embodiment of the present disclosure will be briefly introduced.

a) Add a raw acid from an adding funnel, and observe change in liquid level until an appropriate liquid level is reached.

b) Run software in the host computer, set a heating temperature (not higher than a boiling point) and time, click a "start" button, and then the heater starts heating.

c) The temperature sensor continuously collects a temperature signal of the acid liquid, and sends the same to the computer, the software automatically determines whether or not to continue or stop heating according to the set value and an actual value, so as to keep the temperature of the acid liquid stable at the set value.

d) The raw acid is slowly evaporated at a temperature below a boiling point; the acid steam is condensed by the condenser, and further collected by a pure acid collection rack. The collected acid liquid goes through a drainage tube into the collection bottle.

e) When a set running time is reached, the program automatically stops, and the whole process is completed.

f) During a running process of the program, the raw acid liquid level controller continuously collects change of the liquid level of the raw acid liquid and sends the same to the computer; when a preset minimum value is reached, the program will be terminated automatically.

g) During the running process of the program, the pure acid liquid level controller continuously collects change of weight of the collection bottle, and sends the same to the computer; when a preset maximum value is reached, the program will be terminated automatically.

Hereinafter, structures and working principles of respective components according to the embodiments of the present disclosure will be described with reference to the accompanying drawings.

I: Embodiment 1: Integrated Liquid Level Control Component for an Acid to be Purified According to the embodiment of the present disclosure, the purifier is provided with an integrated liquid level control component for the acid to be purified.

Figure 3:
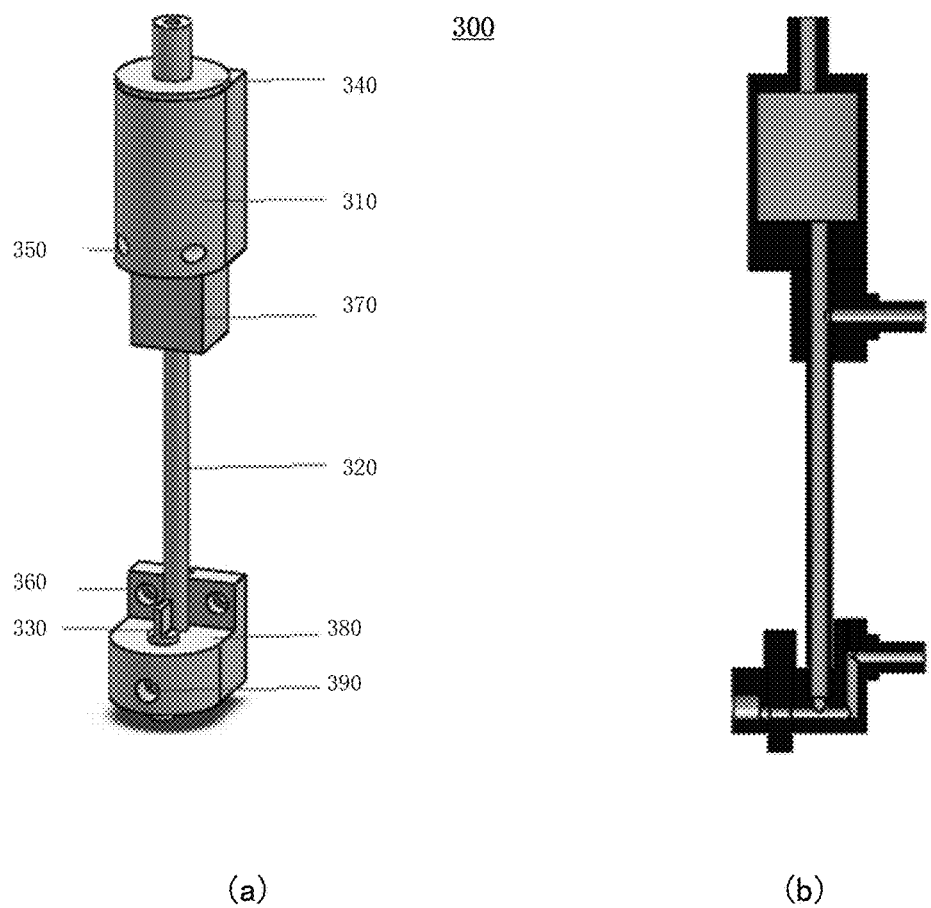
FIG. 3(a) and FIG. 3(b) respectively show a tridimensional view and a cross-sectional view of an integrated liquid level control component 300 of an acid to be purified according to an embodiment of the present disclosure.

FIG. 3(a) and FIG. 3(b) respectively show a tridimensional view and a cross-sectional view of an integrated liquid level control component 300 (which may be, for example, as Portion E shown in FIG. 1) of an acid to be purified according to an embodiment of the present disclosure. The integrated liquid level control component 300 for the acid to be purified is arranged in such a way that an adding funnel 310, a liquid level tube 320 and a waste liquid discharge valve 330 are integrated, the acid to be purified enters the inside of the container for the acid to be purified through the adding funnel 310; a liquid level of the liquid level tube 320 reflects a liquid level of the container for the acid to be purified; and the waste liquid discharge valve 330 can discharge the waste liquid when it is opened.

A lid 340 covers the adding funnel 310, fixing screw holes 350 and 360 are used for fixing the integrated liquid level control component 300 for the acid to be purified onto the container 1 for the acid to be purified as shown in FIG. 2 with screws.

Reference signs 370 and 380 respectively denote an upper interface portion and a lower interface portion, communicated with the inside of the container for the acid to be purified. A reference sign 390 denotes a waste liquid discharge port; when the waste liquid discharge valve 330 is opened, solution in the container for the acid to be purified is discharged from the waste liquid discharge port 390 through the lower interface portion 380.

The integrated liquid level control component 300 for the acid to be purified according to this embodiment may integrally implement functions of liquid adding, liquid discharging and liquid level monitoring, specifically:

Liquid adding: the lid 340 is opened, the raw acid liquid is poured into the adding funnel 310, and the liquid enters the interior of the acid purifier body through an upper path and a lower path communicatively connected with the upper interface portion 370 and the lower interface portion 380.

Liquid discharging: by rotating the discharge valve by 90°, the waste liquid will be discharged from the waste liquid discharge port 390.

Liquid level: by observing the liquid level tube 320, a current liquid level condition can be visualized.

The integrated liquid level control component 300 for the acid to be purified according to this embodiment integrates the liquid level tube, the adding funnel and the waste liquid discharge valve into one, so that it not only can observe change of the liquid level, but also can serve as a funnel to add the liquid, and can discharge a waste liquid as well, which avoids a trouble that the funnel needs to be installed and uninstalled before and after adding the acid liquid, in a conventional solution that the funnel, the liquid level pipe and the waste liquid discharge valve are separated from each other, so as to avoid pollution in a funnel storage process.

II. Embodiment 2: Built-in Temperature Sensor Device

As described above, in a conventional purifier, in order to prevent the temperature sensor from being easily corroded by high temperature strong acid, all temperature sensors are installed outside a container, to avoid contact with the strong acid; however, in such an installation mode, it is temperature of an outer wall of the container that is measured, which cannot reflect true temperature of the acid liquid, usually there is a difference of 5° C. to 20° C. between temperature of a solution and temperature of the outer wall of the container, a temperature measurement error is great; however, in the conventional solution, a temperature controller is a multi-position type, rather than a continuously adjustable type, which may only set a temperature value roughly and cannot set accurately.

According to the embodiment of the present disclosure, there is provided a built-in temperature sensor device, wherein, the temperature sensor is directly placed in an acid liquid. The controller sets a temperature threshold, receives the temperature measured by the acid liquid temperature sensor, compares the temperature with the temperature threshold, and controls the heater accordingly.

In one example, a thermocouple-type temperature sensor and auxiliary parts are used. The temperature sensor device according to this embodiment needs to solve two problems: 1. the thermocouple lead and the thermocouple head cannot be in direct contact with the acid liquid; 2. temperature of a medium in contact with the thermocouple head should be equal to or substantially equal to temperature of the acid liquid.

In one example, a capillary thermocouple lead (e.g., with an outer diameter of about 0.8 mm) is used for threading the thermocouple into a polytetrafluoroethylene (PTFE) capillary with an inner diameter of, e.g., about 1 mm, then the PTFE capillary passes through an inner hole of a support tube, is wound around a tube coiler for one circle and enters into the support tube, and then two PTFE capillaries extends out of a barrel through a connection hole on a wall of the acid purifier.

In one example, two thermocouple leads may be placed in a polytetrafluoroethylene (PTFE) capillary, the PTFE capillary is placed in the support tube, the support tube is placed in the container for the acid to be purified, and the PTFE capillary extends outside the container for the acid to be purified through a connection hole on a wall of the container for the acid to be purified.

In one example, a lower end of the support tube is connected with a tube coiler, and the PTFE capillary inside the support tube passes through the inner hole of the support tube and then gets out, is wound around the tube coiler for one circle and enters into the support tube through a hole of the support tube, then extends upward along the support tube, and finally passes through the hole of the support tube and the connection hole on a wall of the container for the acid to be purified, to extend outside the container for the acid to be purified, wherein, a thermocouple head portion is located within the one circle for which the PTFE capillary is wound, and the thermocouple head portion is in contact with the PTFE capillary.

In one example, the two thermocouple leads may be brought into contact oppositely, seemingly as one lead, and the portions in opposite contact become a thermocouple head.

Figure 4:
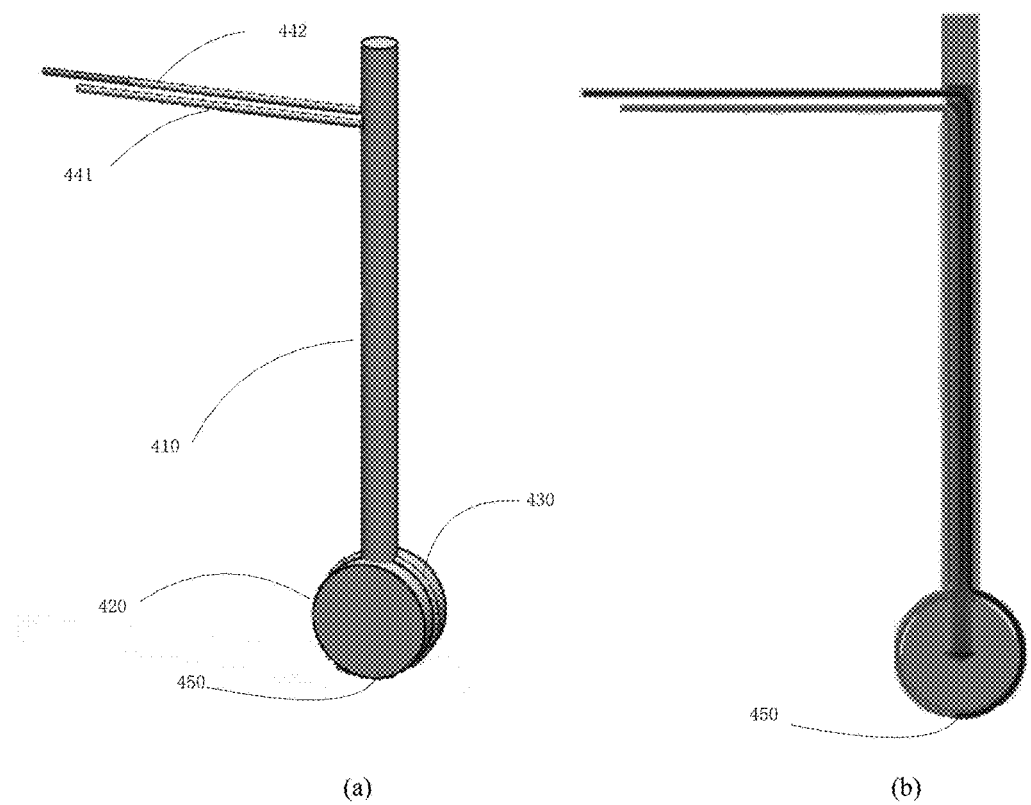
FIG. 4(a) and FIG. 4(b) respectively show a tridimensional schematic diagram and a cross-sectional view of a thermocouple-type temperature sensor device 400 according to one embodiment of the present disclosure.

FIG. 4(a) and FIG. 4(b) respectively show a tridimensional view and a cross-sectional view of a thermocouple-type temperature sensor device 400 according to one embodiment of the present disclosure.

A reference sign 441 indicates, for example, a portion of a thermocouple conduction wire that enters the support tube 410, which is externally fitted with a polytetrafluoroethylene (PTFE) capillary. A PTFE material may withstand high temperature of 250° C. and corrosion of strong acids and strong bases, equivalent to coating a protective film on the thermocouple, which plays a role in anti-corrosion. Here the PTFE material may be replaced by other materials resistant to high temperature, and corrosion of strong acids and strong bases.

The thermocouple conduction wire then extends downward along the support tube 410, extends out of an outlet (not shown) on the support tube 410 close to a wall of the tube coiler 420, is wound around the tube coiler 420 for one circle, enters into the support tube 410 through an inlet (not shown) on the support tube 410, then extends upward along the support tube 410, finally extends out of an upper outlet (not shown) on the support tube 420, and then the portion 442 extending out of the support tube 420 extends out of the purifier through the connection hole on the wall of the purifier. A thermocouple sensing head 450 is located within the one circle for which the PTFE capillary is wound on the wall of the tube coiler 420, for example, just below the wall of the tube coiler 420 as shown in the diagram, so as to be in contact with the acid liquid. By means of circular revolution of the tube coiler, it is possible to avoid a problem that the PTFE capillary is easily broken caused by direct folding.

In order that temperature sensed by the thermocouple sensing head is the temperature of the acid liquid, diameters of the thermocouple lead and the PTFE capillary are so designed that the thermocouple lead and the PTFE capillary are brought into close contact, for example, diameter difference between the PTFE capillary and the thermocouple lead is smaller than 2 mm, preferably less than 1 mm, and more preferably, less than 0.5 mm.

Figure 5:
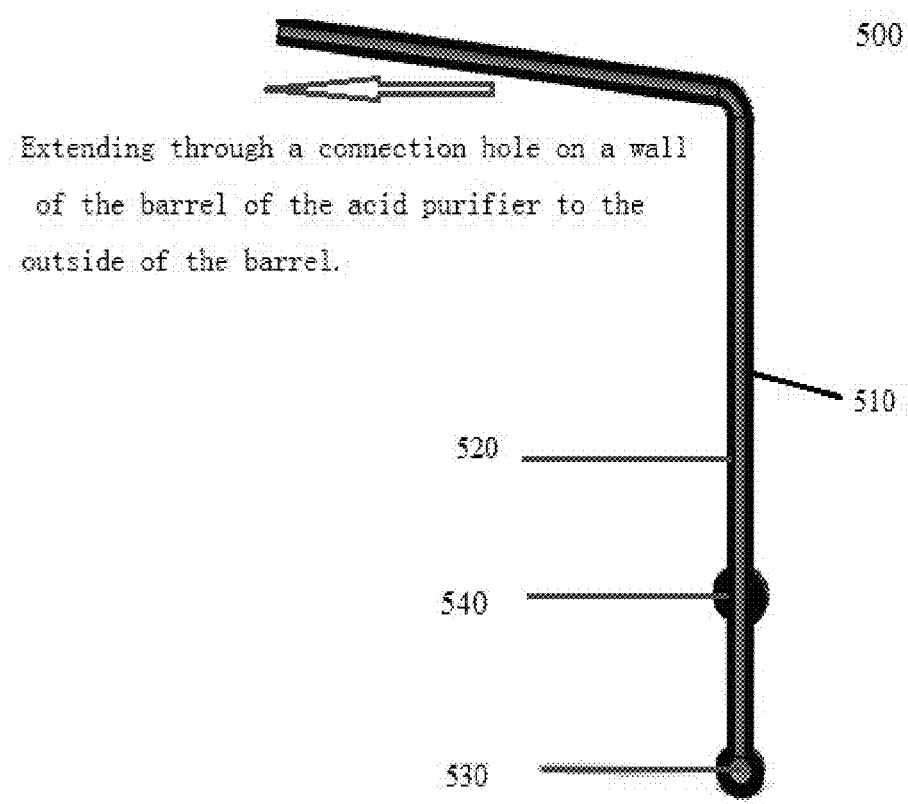
FIG. 5 shows a tridimensional schematic diagram of a thermocouple-type temperature sensor 500 according to an embodiment of the present disclosure.

FIG. 5 shows a tridimensional schematic diagram of a thermocouple-type temperature sensor 500 according to another embodiment of the present disclosure.

As shown in FIG. 5, (two) thermocouple leads 510 are enveloped by a PTFE envelope layer 520. Temperature of a medium in direct contact with a thermocouple sensing head, i.e., a thermocouple probe 530, should be equal to or substantially equal to temperature of an acid liquid; to this end, the thermocouple sensing head should be brought into close contact with the PTFE envelope layer; since the PTFE envelope layer is in direct contact with the acid liquid, it may be deemed that temperature of the PTFE envelope layer is equal to the temperature of the acid liquid. In order to ensure that the thermocouple sensing head is in close contact with the PTFE envelope layer, in an example shown in FIG. 5, a thermo-compression method is used in a position of the thermocouple sensing head, i.e., the thermocouple probe, so that the probe is perfectly bond to the PTFE wall. Further, in order to prevent interference caused by external cold air entering inside, a plurality of sealing points 540 are designed on the lead, and are also sealed by using the thermo-compression method.

The thermocouple conduction wire is, for example, a capillary thermocouple conduction wire, for example, a surface of a thermocouple with an outer diameter of about 0.8 mm is enveloped with a PTFE envelope layer with a wall thickness of about 0.5 mm. A PTFE material can withstand 250° C. high temperature and corrosion of strong acids and strong bases, equivalent to coating a protective film on the thermocouple, which plays a role in anti-corrosion. In addition, the position of the probe is fully integrated with the thin wall by using the thermo-compression method, so that temperature measurement is more accurate and faster.

III. Embodiment 3: Condenser, Semiconductor Cooler, Pure Acid Temporary Collection Device and Heater As described above, a conventional purifier uses a mode of air-cooling or tap water cooling. Both modes show no temperature indicating a cooling effect; in addition, both modes are susceptible to influence of air temperature and tap water temperature conditions; once the air temperature or the water temperature rises, the cooling effect will be affected; moreover, a tap water cooling mode also has a risk of incapability of cooling down due to a lack of water supply.

The condenser according to the embodiment of the present disclosure includes a Peltier semiconductor cooler, a condenser body, a refrigerant temperature sensor, wherein, "cold water" cooled in the Peltier semiconductor cooler, enters the condenser body by pressure of a water pump, to cool the acid steam in contact with an outer shell of the condenser body, "hot water" then enters into the Peltier semiconductor cooler through the water pump to be cooled, and then the process restarts and works circularly; and the refrigerant temperature sensor measures temperature of a refrigerant in the Peltier semiconductor cooler.

Figure 6:
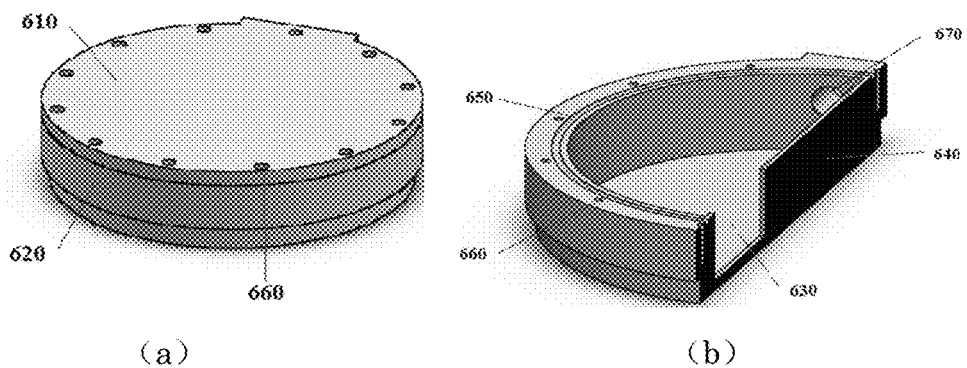
FIG. 6 shows a structural example of a condenser body 600 according to an embodiment of the present disclosure.

FIG. 6 shows a structural example of a condenser body 600 according to an embodiment of the present disclosure. The condenser body 600 includes a lid portion 610, an intermediate body 620, a diaphragm 630 and a baffle 640.

The lid portion 610 and the intermediate body 620 are sealed with a seal ring 650 therebetween. The lid portion 610 is made of, for example, a PVDF material, and the seal ring 650 is, for example, a silicone seal ring. A reference sign 660 denotes a screw hole for fixing the lid, and a reference sign 670 denotes a cooling water inlet.

The bottom of the condenser body 600 is a diaphragm 630 having a thickness less than a predetermined threshold; the diaphragm is in contact with the hot acid steam (which is obtained, for example, by heating the acid solution to be purified with the heater 2 as shown in FIG. 1), to cool the hot acid steam; the condensed purified acid enters the purified acid liquid collection bottle through a drainage tube (for example, as indicated by reference sign 3 shown in FIG. 1).

A middle portion of the condenser body is divided into two portions by a baffle 640, to guide a direction of water flow, so that internal temperature is more uniform.

On tubing between the Peltier semiconductor cooler (not shown in FIG. 6) and the condenser body 600, a refrigerant temperature sensor (not shown in FIG. 6), for example, a capillary thermocouple, is inserted into the tubing and an insertion port is subjected to seal processing, which ensures no seepage of the refrigerant. This design may ensure that the thermocouple detects actual temperature of the refrigerant, rather than temperature of the outer wall of the tubing. The capillary thermocouple, for example, has a diameter of about 1.0 mm, which is easy for bending.

With respect to a problem that the acid purifier operates in a highly corrosive environment for a long period of time, and the Peltier semiconductor cooler is susceptible to corrosion of acid gas, in one example, the semiconductor cooler is placed outside the fume hood (it should be noted that, the purifier body is typically placed within the fume hood), so as to avoid contact with the acid gas. In one example, the condenser body (also referred to as a heat exchanger) is made of a PTFE material, and the refrigerant cooled by the semiconductor refrigerator exchanges heat with the acid steam on both sides of the bottom diaphragm 630 of the condenser body, the refrigerant after heat exchange is pumped into the cooler to be re-cooled, and the process is repeated again and again.

The pure acid liquid condensed by the condenser is generally collected briefly and then drained into the collection bottle.

Figure 7:
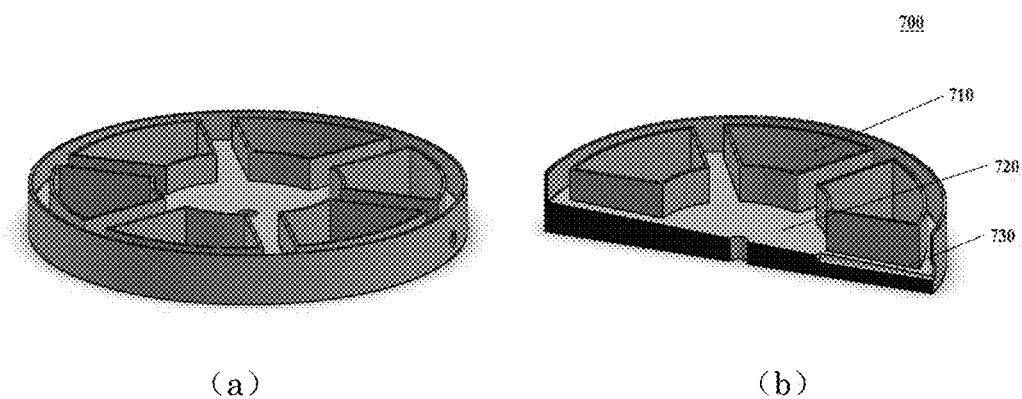
FIG. 7(a) and FIG. 7(b) show a structural schematic diagram and a cross-sectional view of a pure acid temporary collection device 700 according to the embodiment of the present disclosure.

FIG. 7(a) and FIG. 7(b) show a structural schematic diagram and cross-sectional view of a pure acid temporary collection device 700 according to the embodiment of the present disclosure.

The acid steam, through an ascending port 710 on the pure acid temporary collection device 700 (or referred to as the collection bottle), ascends to the diaphragm of the condenser body, and then is cooled, the condensed pure acid liquid flows back from the diaphragm along a barrel wall of the collector or directly drips down onto a collection tray 720. An upper surface of the collection tray 720 is designed to be inclined so that the pure acid liquid collects in a draining port 730 under gravity, and enters the collection bottle through the drainage tube.

Hereinafter, the heater for heating the acid to be purified according to the embodiment of the present disclosure is described.

As described above, an infrared lamp or a resistance wire is used as a heat source for the purifier in the prior art, which is open flame and easily ignites inflammable gas around; once the temperature controller fails, the infrared lamp or the resistance wire will continue to heat, causing a great risk of burning down an instrument or even a laboratory fire.

A purifier according to one embodiment of the present disclosure uses a PTC heater, due to a positive temperature coefficient (PTC) effect, current flows through the element to cause temperature rise, that is, temperature of a heating element rises; once the temperature exceeds a certain temperature (Curie temperature), its resistance value increases with temperature almost step-wisely, so as to limit current increase, and thus, current drop causes element temperature to drop. However, drop of the temperature will make the resistance decrease, so that circuit current increases, and element temperature increases, and then the process restarts and works circularly, so as to keep the temperature in a specific range. When the PTC heater generates heat, it does not become red, without any open flame, and is not inflammable. Even if the temperature controller fails, the PTC heater will not continue to heat over the Curie temperature and will not generate any combustion danger.

According to a preferred embodiment of the present disclosure, with respect to the problem that the acid purifier operates in the highly corrosive environment for a long period of time, and the PTC heater is easily corroded by the acid gas, the heater is specifically designed to include any of the following, but not limited thereto, and can also be designed in any other ways:

(1) The PTC heater itself is subjected to surface spraying of PTFE, which can effectively resist corrosion of acid liquid and acid gas;

(2) The body and the base of the acid purifier use a nested connection design, to form a closed space between the two, and the entire PTC heater is installed inside the closed space, so that the entire PTC heater is enveloped by the body and the base, so as to eliminate contact with the external acid gas;

(3) In addition, in consideration of uniformity of heating, a thermal conductive pad having a smaller thickness of, for example, 3 mm, and an area far larger than a heating surface of the PTC heater, is specially designed, the thermal conductive pad is closely bond to the bottom of the acid purifier, to perform heat thermal conduction, which can effectively improve a problem of uneven heat transfer due to a fact that the PTC heater cannot completely be bond to the acid purifier body. The thermal conductive pad may be made of a pure aluminum material with a very good thermal conductivity, and may also be subjected to surface spraying of PTFE.

Figure 8:
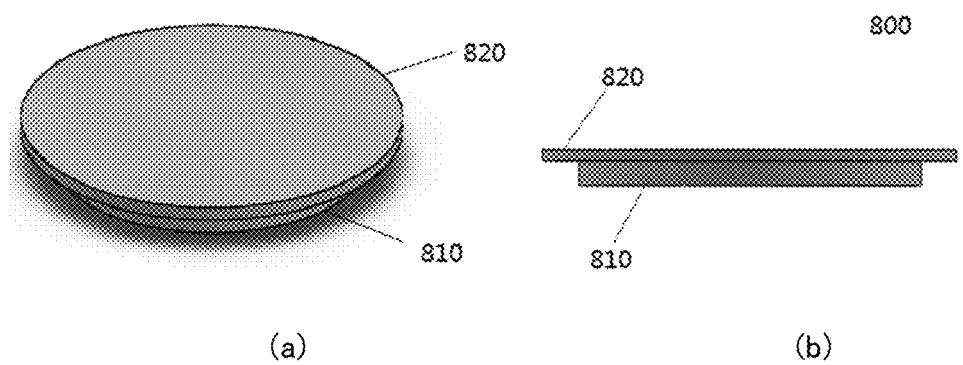
FIG. 8(a) and FIG. 8(b) show a tridimensional view and a cross-sectional view of a structure of a heater 800 according to one embodiment of the present disclosure.

FIG. 8(a) and FIG. 8(b) show a tridimensional schematic diagram and a cross-sectional view of a heater 800 according to one embodiment of the present disclosure.

As shown in FIG. 8(a) and FIG. 8(b), the heater 800 includes a PTC heater body 810 and a thermal conductive pad 820. An area of the thermal conductive pad 820 is much larger than an area of the PTC heater body 810, preferably, the former is equal to or greater than 1.5 times the latter. The area of the thermal conductive pad 820 may be designed according to an area of the bottom of the acid purifier body, for example, the two have a same area; in addition, the bottom surface of the thermal conductive pad 820 and the top surface of the PTC heater body 810 are in close contact with each other to perform heat conduction so as to effectively improve a problem of uneven heat transfer due to a fact that the PTC heater cannot completely be bond to the entire bottom of the acid purifier body.

VI. Embodiment 4: Non-Contact Liquid Level Sensor for Acid to be Purified

As described above, in the purifier of the prior art, there is no liquid level sensor. In consideration that the acid purifier operates at high temperature (above 100° C.) for a long period of time, if the liquid level sensor is installed closely against an outer wall of a container, the liquid level sensor closely against the outer wall of the container is easily overheated to fail or be damaged. According to one embodiment of the present disclosure, a raw acid liquid level sensor of the purifier uses a non-contact ultrasonic liquid level sensor; the device automatically senses liquid level change, once the liquid level is lower than a set value, it sends a voltage signal to a software, the software automatically shuts down, which avoids personnel negligence and major fire hidden danger; in addition, the special liquid level sensor according to the embodiment of the present disclosure, has its measured surface not in direct contact with the outer wall of the container and maintains a certain space, for example, 2 mm, which not only avoids the problem of failure or damage due to rapid accumulation of heat, but also avoids the problem of loss of due sensitivity because the measured surface is too far away from the solution.

Figure 9:
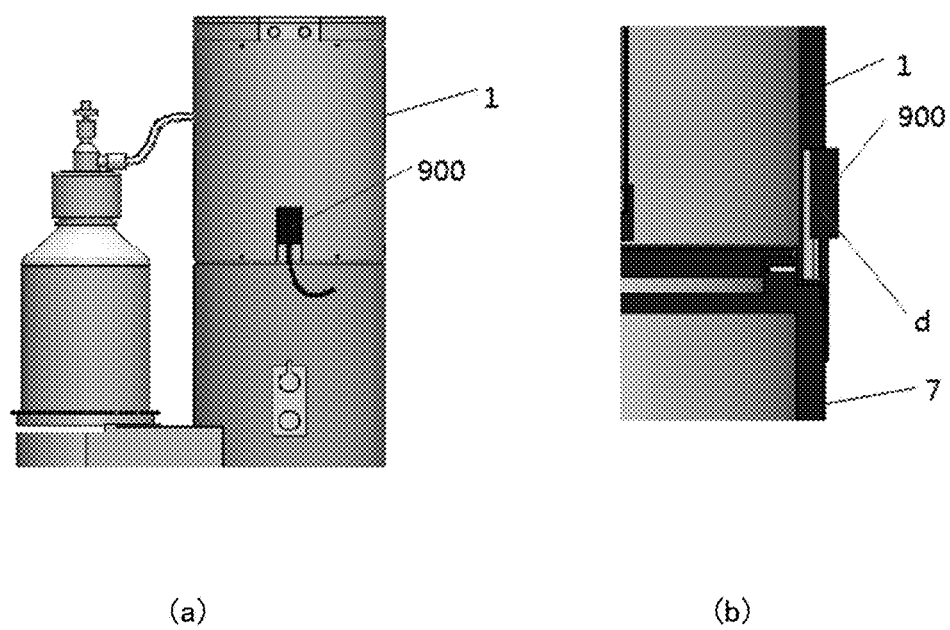

FIG. 9 (a) and FIG. 9(b) show a tridimensional view and a cross-sectional view of a purifier provided with an ultrasonic liquid level sensor 900 according to an embodiment of the present disclosure.

As shown in FIG. 9 (b), the ultrasonic liquid level sensor 900 is installed on an outer surface of the container 1 for the acid to be purified, and there is a distance d between the ultrasonic liquid level sensor 900 and a wall surface of the container 1 for the acid to be purified, where d is greater than zero. A reference sign 7 indicates an outer shell of the purifier.

The purifier according to the embodiment of the present disclosure uses a non-contact specially-designed ultrasonic infrared liquid level sensor, which is installed on the outer surface of the container, and is not in contact with the surface of the container, which not only avoids the problem that the sensor is in direct contact with the acid liquid so as to be corroded, but also avoids the problem that the sensor is in direct contact with the high-temperature container, so as to cause circuit damage.

Hereinafter, a pressure sensor for indirectly sensing a pure acid liquid level according to an embodiment of the present disclosure is described below with reference to the accompanying drawings.

Figure 10:
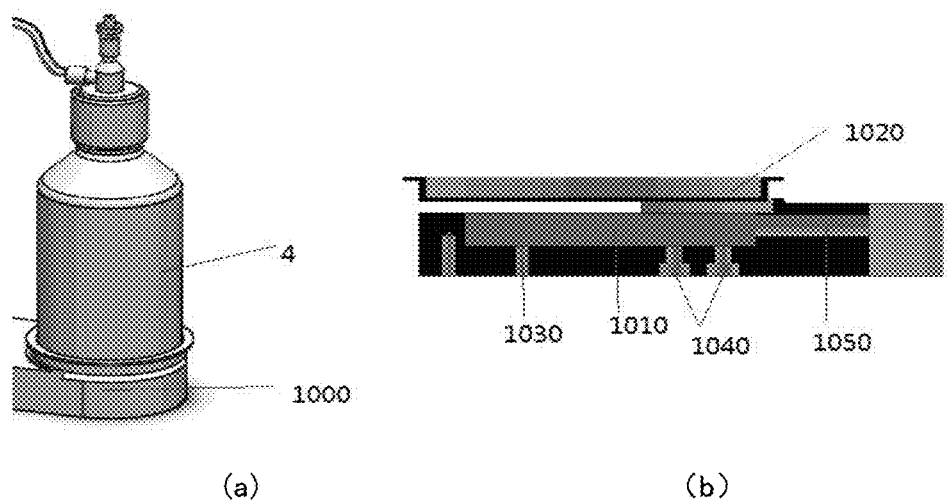
FIG. 10 (b) shows a cross-sectional view of the pressure sensor and the relevant portion 1000 according to the embodiment of the present disclosure.

FIG. 10(a) shows a tridimensional schematic diagram of relative position relation between a pure acid solution collection bottle 4 and the pressure sensor and a relevant portion 1000 according to the embodiment of the present disclosure, FIG. 10 (b) shows a cross-sectional view of the pressure sensor and the relevant portion 1000 according to the embodiment of the present disclosure.

According to an embodiment of the present disclosure, the pressure sensor is a pressure sensor of a weight resistive strain type, the weight pressure sensor continuously collects pressure changes caused by a weight of the collection bottle and sends the same to the computer; when the weight reaches a preset maximum value, an acid purification process will be terminated automatically, which avoids personnel negligence and major hidden danger of chemical corrosion.

In one example, a tray 1020 is placed under the collection bottle 4, preferably, the tray 1020 is designed in a flanging manner, capable of containing about 20 mL of dripped acid liquid, to prevent turbulent flow of the acid liquid, and prevent dripping of the acid liquid into the interior of the sensor. In one example, the sensor 1010 is, for example, designed with a leak outlet 1030 at its rack, so that the acid liquid may be drained in time just in case that the acid liquid enters the sensor.

The pressure sensor 1010 and/or other portions, for example, the tray, a sensor fixing screw hole 1040 and a data line hole 1050 may be subjected to surface spraying of PTFE or be made of a PTFE material themselves to prevent acid corrosion.

According to one embodiment of the present disclosure, data collected by all the sensor and instructions transmitted by the computer software may be transmitted via Bluetooth or Wifi, and the controller (the host computer and the slave computer) may be placed outside the fume hood, which saves space for the fume hood, and allows the personnel to perform remote control.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. Any variations or replacements capable of being easily thought by those skilled in the art shall fall within the scope of the present disclosure.

The invention claimed is:

1. An acid purifier, comprising:
    a container for an acid to be purified, for containing the acid to be purified;
    a heater, for heating the container for the acid to be purified, to obtain hot acid steam;
    a condenser, configured to condense the hot acid steam;
    a purified acid liquid collection bottle connected with the condenser, for collecting condensed purified acid;
    a controller, for controlling operation of respective components so as to perform an acid purification process;
    an acid liquid temperature sensor, arranged in the acid to be purified, for measuring temperature of the acid liquid to be purified;
    wherein, the controller sets a temperature threshold, receives the temperature measured by the acid liquid temperature sensor, compares the temperature with the temperature threshold, and correspondingly controls the heater,
    wherein, the acid liquid temperature sensor is a thermocouple-type temperature sensor, two thermocouple leads are placed in a polytetrafluoroethylene (PTFE) capillary, the PTFE capillary is placed in a support tube, the support tube is placed in the container for the acid to be purified, and the PTFE capillary extends to the outside of the container for the acid to be purified through a connection hole on a wall of the container for the acid to be purified,
    wherein, the lower end of the support tube is connected with a tube coiler, and the PTFE capillary inside the support tube passes through an inner hole of the support tube and gets out, winds around the tube coiler for one circle and enters into the support tube through a hole of the support tube, then extends upward along the support tube, and finally passes through the hole of the support tube and the connection hole on the wall of the container for the acid to be purified, to extend outside the container for the acid to be purified,
    wherein, a thermocouple head portion is located within the one circle for which the PTFE capillary is wound, and the thermocouple head portion is in contact with the PTFE capillary,
    the two thermocouple leads are brought into contact oppositely, forming one lead, and the portions in opposite contact form the thermocouple head portion,
    wherein, the surface of the thermocouple lead is enveloped by a PTFE envelope layer, and at the position of the thermocouple probe, a thermo-compression method is used for tightly bonding the thermocouple probe to the PTFE envelope layer,
    wherein, one or more sealing points are present on the thermocouple lead, and a thermo-compression method is used at the sealing point for tightly bonding the thermocouple lead to the PTFE envelope layer.

2. The acid purifier according to claim 1, wherein, the controller is capable of continuously setting temperature thresholds.

3. The acid purifier according to claim 1, wherein,
    the condenser includes a Peltier semiconductor cooler, a condenser body, and a refrigerant temperature sensor,
    "cold water" cooled in the Peltier semiconductor cooler enters the condenser body by pressure of a water pump, to cool the acid steam in contact with the outer shell of the condenser body, "hot water" then enters into the Peltier semiconductor cooler through the water pump to be cooled, and then the process restarts and works circularly; and the refrigerant temperature sensor measures the temperature of a refrigerant in the Peltier semiconductor cooler.

4. The acid purifier according to claim 3, wherein,
a bottom of the condenser body is a diaphragm having a thickness less than a predetermined threshold; the diaphragm is in contact with the hot acid steam to cool the hot acid steam; the condensed purified acid enters the purified acid liquid collection bottle through a drainage tube.

5. The acid purifier according to claim 3, wherein,
a middle portion of the condenser body is divided into two portions by a baffle, to guide a water flow direction, so that the temperature of the refrigerant is more uniform.

6. The acid purifier according to claim 3, wherein, the refrigerant temperature sensor uses a capillary thermocouple; on tubing between the semiconductor cooler and the condenser body, the capillary thermocouple is inserted into the tubing and an insertion port is subjected to seal processing.

7. The acid purifier according to claim 3, the purifier is placed inside a fume hood, and the semiconductor cooler and the controller are placed outside the fume hood.

8. The acid purifier according to claim 1, further comprising:
a non-contact ultrasonic liquid level sensor, installed on an outer surface of the container and not in contact with a surface of the container, for automatically measuring a liquid level of the acid to be purified in the container for the acid to be purified, and sending a measured signal indicating the liquid level to the controller, wherein, the controller receives the signal indicating the liquid level, and sends a control signal when the signal indicating the liquid level is below a predetermined threshold, so as to control stopping the acid purification process.

9. The acid purifier according to claim 1, further comprising:
a pressure sensor, for automatically sensing weight of the purified acid liquid collection bottle, and sending a signal indicating the weight to the controller;
wherein, the controller receives the signal indicating the weight, and sends a control signal when the signal indicating that the weight exceeds a predetermined threshold, so as to control stopping the acid purification process.

10. The acid purifier according to claim 9, wherein:
the purified acid liquid collection bottle is placed on a tray, the tray is designed in a flanging manner, to prevent the acid liquid from dripping into the pressure sensor; and
the pressure sensor is designed with a leak outlet, to allow the acid liquid to be discharged in a case where there is an acid liquid entering inside the pressure sensor.

11. The acid purifier according to claim 9, wherein:
the pressure sensor is subjected to surface spraying of PTFE.

12. The acid purifier according to claim 9, wherein:
the heater is a PTC heater.

13. The acid purifier according to claim 9, wherein:
the controller includes a computer as a host computer and a microcontroller as a slave computer, and
data transmission between all sensors and computers is performed by means of wireless communication.

* * * * *